(12) United States Patent
Nishizaki et al.

(10) Patent No.: US 7,468,389 B2
(45) Date of Patent: Dec. 23, 2008

(54) CARBOXYLIC ACID COMPOUND HAVING CYCLOPROPANE RING

(75) Inventors: Tomoyuki Nishizaki, Kobe (JP); Akito Tanaka, Osaka (JP)

(73) Assignees: Tox K.K., Kobe-shi (JP); Tomoyuki Nishi, Kobe-shi (JP)

(*) Notice: Subject to any disclaimer, the term of this patent is extended or adjusted under 35 U.S.C. 154(b) by 0 days.

(21) Appl. No.: 10/450,816

(22) PCT Filed: Dec. 18, 2001

(86) PCT No.: PCT/JP01/11066

§ 371 (c)(1),
(2), (4) Date: Jun. 18, 2003

(87) PCT Pub. No.: WO02/50013

PCT Pub. Date: Jun. 27, 2002

(65) Prior Publication Data

US 2005/0075393 A1     Apr. 7, 2005

(30) Foreign Application Priority Data

Dec. 19, 2000   (AU) .................................... PR2157

(51) Int. Cl.
*A61K 31/215* (2006.01)
*C07C 61/00* (2006.01)
*C07C 61/04* (2006.01)

(52) U.S. Cl. .................. 514/531; 562/506; 562/510

(58) Field of Classification Search .................. 562/506, 562/510; 514/531
See application file for complete search history.

(56) References Cited

U.S. PATENT DOCUMENTS 4,001,428 A   1/1977   Kosower et al.
4,442,099 A   4/1984   Nicolaou et al.

(Continued)

FOREIGN PATENT DOCUMENTS

JP   57 095937   6/1982

(Continued)

OTHER PUBLICATIONS

G.D. Coxon et al.: "The synthesis of both enantiomer of lactobacillic acid and mycolic acid analogues" Tetrahedron Letters, vol. 40, No. 36, pp. 6689-6692.

(Continued)

*Primary Examiner*—Taylor Victor Oh
(74) *Attorney, Agent, or Firm*—Oblon, Spivak, McClelland, Maier & Neustadt, P.C.

(57) ABSTRACT

A carboxylic acid compound having cyclopropane ring(s) of the formula (I): wherein R is alkyl or alkenyl optionally having one or more 1,2-cyclopropylene in a carbon chain and/or optionally having cyclopropyl at the end of a chain, X is a single bond or alkylene, wherein the total number of carbon less the number of cyclopropane ring is 10-25, and a pharmaceutically acceptable salt thereof are provided. The compound (I) shows an LTP-like potentiation of synaptic transmission, allows slow metabolism in the living body, show a stable LTP-like potentiation of synaptic transmission, and is useful as an agent for LTP-like potentiation of synaptic transmission, a cognition-enhancing drug or an agent for the prophylaxis and treatment of dementia, a learning and memory disorder and a neurotransmitter release disorder.

8 Claims, 1 Drawing Sheet

U.S. PATENT DOCUMENTS

| | | |
|---|---|---|
| 4,562,006 A | 12/1985 | Connor et al. |
| 5,973,111 A | 10/1999 | Bemis et al. |
| 5,990,104 A | 11/1999 | Dimaio et al. |
| 6,169,103 B1 | 1/2001 | Purchase, Jr. et al. |
| 6,492,363 B2 | 12/2002 | Barrett et al. |
| 6,831,066 B2 | 12/2004 | Findeis et al. |
| 6,887,898 B1 | 5/2005 | Kim |
| 6,962,913 B2 | 11/2005 | Olson et al. |

FOREIGN PATENT DOCUMENTS

| | | |
|---|---|---|
| JP | 58 194836 | 11/1983 |

OTHER PUBLICATIONS

K. Hofmann et al.: "On the structure of lactobacillic acid" Journal of the American Society, vol. 76, pp. 1799-1804 1954.

Biochim. Biophys. Acta, vol. 210, pp. 495-498 1970.

CARBOXYLIC ACID COMPOUND HAVING CYCLOPROPANE RING

TECHNICAL FIELD

The present invention relates to new carboxylic acid compounds and pharmaceutically acceptable salts thereof, which are useful as medicines.

BACKGROUND ART

In 1973, Bliss et al. elucidated that a tetanic electric stimulation on the perforating fiber having a nerve ending in hippocampal dentate gyrus results in the sustained potentiation of subsequent response to an electric stimulation of dentate gyrus that is a postsynaptic cell. This phenomenon is called an LTP (long-term potentiation) and is recognized as a cell model of learning and memory (T. V. P. Bliss and G. L. Collingridge, Nature Vol. 361, page 31, 1993), wherein it is considered that learning and memory is not stored in a specific RNA or peptide but is based on a long-term potentiation of synaptic transmission efficiency. LTP is considered to be the result of a long-term potentiation of neurotransmission, which is a plasticity forming process model of the central nervous system responsible for learning and memory. LTP is also considered to be involved in the onset of various nervous and mental diseases, such as epilepsy, ischemic encephalopathy, Alzheimer's disease and the like. Therefore, a substance that induces LTP expression has a potential of becoming a therapeutic or preventive drug for these nervous and mental diseases inclusive of dementia.

One of the various factors suspected of being involved in controlling LTP expression is arachidonic acid (J. H. Williams, J. Lipid. Mediat. Cell Signal., Vol. 14, page 331, 1996). Arachidonic acid is an unsaturated fatty acid produced by hydrolysis via prophospholipase $A_2$ of phosphatidylcholine that is one of the membrane lipids, and the interaction with the activating pathway of protein kinase C has been drawing attention as to the involvement into the control of LTP expression (Y. Nishizuka, FASEB J, Vol. 9, page 484, 1995). It has been also suggested that arachidonic acid is involved in LTP-like potentiation of synaptic transmission by prolonging activation of neuronal nicotinic acetylcholine receptors (T. Nishizaki et. al., Molecular Brain Research, vol. 69, pp. 263-272, 1999).

Arachidonic acid is produced in the living body and quickly metabolized. Therefore, a stable effect over a long period of time cannot be expected.

To overcome this problem, a compound having an LTP-like potentiation of synaptic transmission, which allows slow metabolism in the body and which is capable of sustaining a stable LTP-like potentiation of synaptic transmission, has been desired.

SUMMARY OF THE INVENTION

It is therefore an object of the present invention is to provide a novel carboxylic acid compound having cyclopropane ring(s), which shows an LTP-like potentiation of synaptic transmission, allows slow metabolism in the body, is capable of sustaining a stable LTP-like potentiation of synaptic transmission, and which is useful as an agent for LTP-like potentiation of synaptic transmission, a cognition-enhancing drug or an agent for the prophylaxis and treatment of dementia, a learning and memory disorder and a neurotransmitter release disorder, and a pharmaceutically acceptable salt thereof.

Another object of the present invention is to provide a pharmaceutical composition containing the carboxylic acid compound or a pharmaceutically acceptable salt thereof as an active ingredient.

A further object of the present invention is to provide a use of the carboxylic acid compound and a pharmaceutically acceptable salt thereof as an agent for LTP-like potentiation of synaptic transmission, a cognition-enhancing drug, or an agent for the prophylaxis and treatment of dementia, a learning and memory disorder and a neurotransmitter release disorder.

A yet another object of the present invention is to provide a method for the prophylaxis and treatment of dementia, a learning and memory disorder or a neurotransmitter release disorder in human or an animal.

According to the present invention, it has been found that a carboxylic acid compound of the following formula (I) (hereinafter to be referred to as compound (I)) and a pharmaceutically acceptable salt thereof have an LTP-like potentiation of synaptic transmission, allow slow metabolism in the living body, show a stable LTP-like potentiation of synaptic transmission, and are useful as an agent for LTP-like potentiation of synaptic transmission, a cognition-enhancing drug or an agent for the prophylaxis and treatment of dementia, a learning and memory disorder and a neurotransmitter release disorder:

(I)

wherein

R is alkyl or alkenyl optionally having one or more 1,2-cyclopropylene in a carbon chain and/or optionally having cyclopropyl at the end of a chain, in which 1,2-cyclopropylene may have a suitable substituent at the 3-position carbon atom, X is a single bond or alkylene, and the total number of carbon less the number of cyclopropane ring is 10-25.

That is, the present invention provides a carboxylic acid compound having cyclopropane ring(s) of the above-mentioned formula (I) or a pharmaceutically acceptable salt thereof.

Preferably, in the formula (I),

R is alkyl or alkenyl optionally having one or more 1,2-cyclopropylene in a carbon chain and/or optionally having cyclopropyl at the end of a chain.

More preferably,

R is

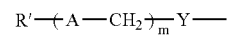

in which R' is hydrogen or alkyl,

Y is a single bond or alkylene,

A is 1,2-cyclopropylene or vinylene, and m is integer from 0 to 5, provided that when m is 2-5, A should be the same or different.

Yet more preferably, R is a group selected from

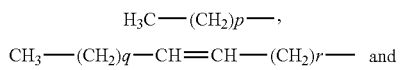
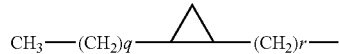
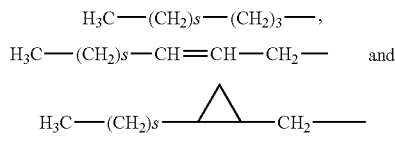

and X is —(CH$_2$)$_n$—,
in which n, p, q and r are each an integer, the total of p and n is from 6 to 21, and the total of q, r and n is from 4 to 19.

Even more preferably, R is a group selected from $$H_3C-(CH_2)s-(CH_2)_3-,$$
$$H_3C-(CH_2)s-CH=CH-CH_2- \quad \text{and}$$
$$H_3C-(CH_2)s-\triangle-CH_2-$$

and X is —(CH$_2$)$_n$—,
in which s and n are each an integer, the total of which being from 3 to 18, and particularly preferably, s is 4 and n is 7.

The present invention also provides a pharmaceutical composition comprising the compound (I) or a pharmaceutical acceptable salt thereof in admixture with a pharmaceutical acceptable carrier.

The present invention further provides a use of the compound (I), such as a medicament (e.g., an agent for LTP-like potentiation of synaptic transmission, a cognition-enhancing drug, or an agent for the prophylaxis and treatment of dementia, a learning and memory disorder and a neurotransmitter release disorder).

DETAILED DESCRIPTION OF THE INVENTION

Figure 1:
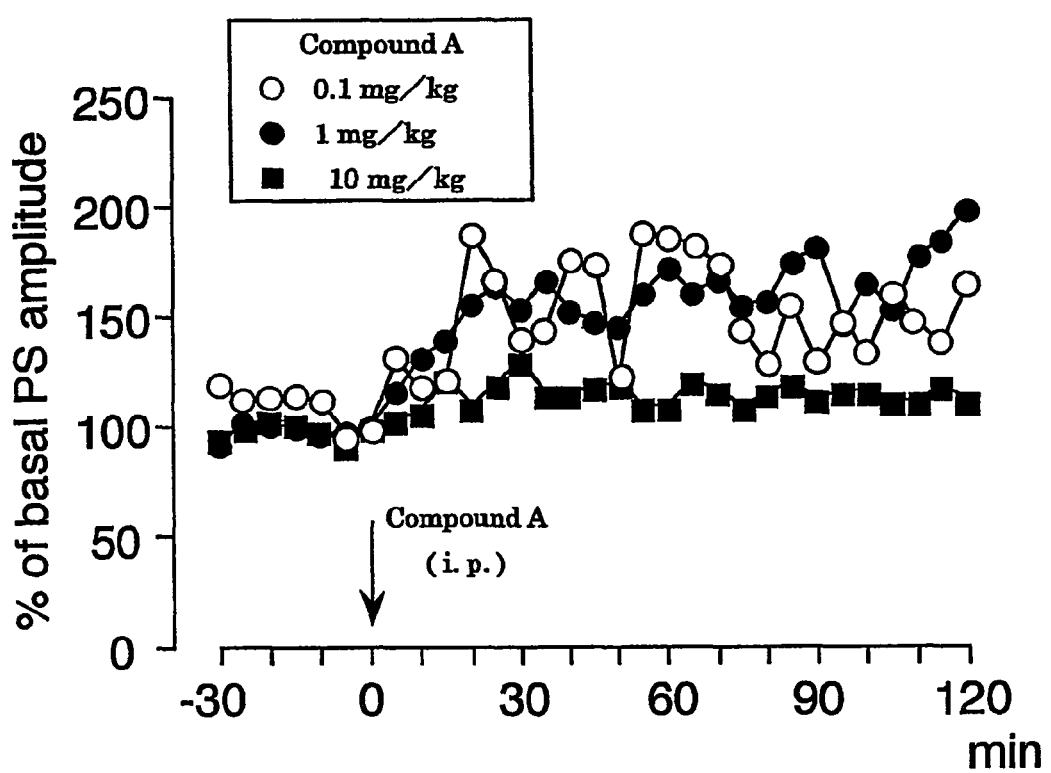
FIG. 1 is a graph showing the LTP-like potentiation of synaptic transmission by Compound A (compound of Example 1) in mice, wherein the abscissa is the lapse of time (min) from the administration of Compound A, the ordinate is the proportion of the PS amplitude at each time point to that before administration of Compound A (percent of basal PS amplitude), ○ shows a value when 0.1 mg/kg (i.p.) of Compound A was administered, ● shows a value when 1 mg/kg (i.p.) of Compound A was administered and ■ shows a value when 10 mg/kg (i.p.) of Compound A was administered.

In the above and subsequent descriptions of the present specification, suitable examples and illustration of the various definitions which the preset invention intends to include within the scope thereof are explained in detail as follows.

In the context of the present invention, an LTP (long-term potentiation) expression means that synaptic transmission efficiency is potentiated over 2 hours or longer by the tetanic stimulation (highly frequent stimulation).

In the context of the present invention, an LTP-like potentiation of synaptic transmission means that synaptic transmission efficiency is potentiated by a certain drug over 2 hours or longer without tetanic stimulation (highly frequent stimulation).

In the context of the present invention, cognition-enhancement means that the cognitive function is improved by increasing the synaptic transmission efficiency.

In the context of the present invention, a neurotransmitter release disorder includes decreased synthesis of neurotransmitters such as acetylcholine, glutamic acid, GABA, noradrenaline, dopamine, serotonin and the like or decreased release of neurotransmitter from presynaptic terminal accompanying degeneration and disappearance of neuron, whose disease state includes Alzheimer's dementia, senile dementia, Parkinson's dementia and the like.

The alkyl at R is straight or branched and includes methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, eicosanyl, docosanyl and the like. The alkyl may have 1,2-cyclopropylene in a carbon chain and/or cyclopropyl at the end of a chain. The presence of 1,2-cyclopropylene in a carbon chain, in the case where alkyl is n-pentyl, means, for example, 2-(2-propylcyclopropan-1-yl)ethyl where 1,2-cyclopropylene is present between the 2-position and 3-position carbon atoms of n-pentyl. Two or more 1,2-cyclopropylene may be present. The presence of cyclopropylene at the end of a chain, in the case where alkyl is n-pentyl, means 5-cyclopropylpentan-1-yl where cyclopropyl is present at the terminal carbon atom (5-position carbon atom) of n-pentyl. The alkyl in the present invention encompasses alkyl having 1,2-cyclopropylene in a carbon chain and cyclopropyl at the end of a chain (e.g., 2-(2-(3-cyclopropylpropyl)cyclopropan-1-yl)ethyl). Examples of alkyl at R, which has 1,2-cyclopropylene in a carbon chain and/or cyclopropyl at the end of a chain, preferably include octyl, (2-pentylcyclopropan-1-yl)methyl, (2-((2-ethyl-cyclopropan-1-yl)methyl)cyclopropan-1-yl) methyl, (2-((2-((2-pentyl-cyclopropan-1-yl)methyl)cyclopropan-1-yl)methyl)cyclopropan-1-yl)methyl, and (2-((2-pentyl-cyclopropan-1-yl)methyl)cyclopropan-1-yl)methyl, with particular preference given to octyl and (2-pentylcyclopropan-1-yl)methyl.

The alkenyl at R is straight or branched and includes ethenyl, propenyl, isopropenyl, butenyl, isobutenyl, sec-butenyl, tert-butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, eicosenyl, docosenyl, butadienyl, pentadienyl, hexadienyl, heptadienyl, octadienyl, nonadienyl, decadienyl, undecadienyl, dodecadienyl, tridecadienyl, tetradecadienyl, pentadecadienyl, hexadecadienyl, heptadecadienyl, octadecadienyl, eicosadienyl, docosadienyl, hexatrienyl, heptatrienyl, octatrienyl, nonatrienyl, decatrienyl, undecatrienyl, dodecatrienyl, tridecatrienyl, tetradecatrienyl, pentadecatrienyl, hexadecatrienyl, heptadecatrienyl, octadecatrienyl, eicosatrienyl, docosatrienyl, octatetraenyl, nonatetraenyl, decatetraenyl, undecatetraenyl, dodecatetraenyl, tridecatetraenyl, tetradecatetraenyl, pentadecatetraenyl, hexadecatetraenyl, heptadecatetraenyl, octadecatetraenyl, eicosatetraenyl, docosatetraenyl and the like. The alkenyl may have 1,2-cyclopropylene in a carbon chain and/or cyclopropyl at the end of a chain. The presence of 1,2-cyclopropylene in a carbon chain, in the case where alkenyl is 1-pentenyl, means, for example, 2-(2-propylcyclopropan-1-yl)ethenyl where 1,2-cyclopropylene is present between the 2-position and 3-position carbon atoms of 1-pentenyl. Two or more 1,2-cyclopropylene may be present. The presence of cyclopropyl at the end of a chain, in the case where alkenyl is 1-pentenyl, means 5-cyclopropyl-1-pentenyl where cyclopropyl is present at the terminal carbon atom (5-position carbon atom) of 1-pentenyl. The alkenyl in the present invention encompasses alkenyl having 1,2- cyclopropylene in a carbon chain and cyclopropyl at the end of a chain, which is exemplified by 2-(2-(3-cyclopropylpropyl)cyclopropan-1-yl)ethenyl. The alkenyl at R having 1,2-cyclopropylene in a carbon chain and/or cyclopropyl at the end of a chain is preferably octenyl.

1,2-Cyclopropylene in R may have a suitable substituent such as alkyl and the like, at the 3-position carbon atom.

Examples of alkyl at the 3-position carbon atom of 1,2-cyclopropylene in R, preferably include methyl, ethyl, propyl, isopropyl, butyl, isobutyl, sec-butyl, tert-butyl, pentyl, tert-pentyl, hexyl and the like.

Alkylene at X is straight or branched and includes methylene, ethylene, propylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene nonadecamethylene, heicosamethylene and the like. Preferred are heptamethylene, trimethylene, tetramethylene.

In compound (I) of the present invention, the total number of carbon less the number of cyclopropane ring should be from 10 to 25, preferably from 18 to 22. The p, q, r, m, n and s are each an integer, inclusive of 0.

A preferable mode of the compound (I) of the present invention is a compound of the formula (I) wherein R is

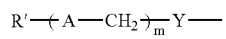

in which R' is hydrogen or alkyl,
Y is a single bond or alkylene,
A is 1,2-cyclopropylene or vinylene,
m is integer from 0 to 5, provided that when m is 2-5, A should be the same or different, A more preferable mode is a compound of the formula (I) wherein
R is a group selected from

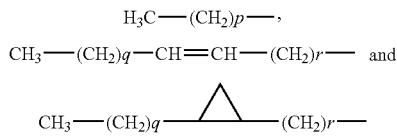

and X is —(CH$_2$)$_n$—,
in which n, p, q and r are each an integer, the total of p and n is from 6 to 21, and the total of q, r and n is from 4 to 19.

A still more preferable mode is a compound of the formula (I) wherein R is a group selected from

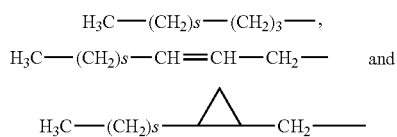

and X is —(CH$_2$)$_n$—, in which s and n are each an integer, the total of which being from 3 to 18. Particularly preferable mode of the compound (I) of the present invention is a compound of the formula (I) wherein s is 4 and n is 7.

The compound (I) of the present invention can be produced by the methods shown in Examples 1 to 6 to be mentioned later.

It is to be noted that the compound (I) may include one or more stereoisomer(s) such as optical isomer(s) and geometrical isomer(s) due to asymmetric carbon atom(s) and double bond(s), and all of such isomers and mixtures thereof are included within the scope of this invention.

The compounds (I) and pharmaceutically acceptable salts thereof include solvates [e.g., enclosure compounds (e.g., hydrate, etc.)].

Suitable pharmaceutically acceptable salts of the object compound (I) are conventional non-toxic salts and include, for example, a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); and a salt with a basic amino acid (e.g. arginine, etc.).

The compounds (I) and pharmaceutically acceptable salts thereof show LTP-like potentiation of synaptic transmission. Therefore, they are useful as an agent for LTP-like potentiation of synaptic transmission; a cognition-enhancing drug; and an agent for the prophylaxis and treatment of various diseases including dementia (e.g., senile dementia, Alzheimer's dementia, dementia caused by various diseases such as cerebrovascular dementia, posttraumatic dementia, dementia caused by brain tumor, dementia caused by chronic subdural hematoma, dementia caused by normal pressure hydrocephalus, post-cephalomeningitic dementia and Parkinson's dementia), learning and memory disorder (e.g., learning and memory disorder associated with disturbance of brain development), neurotransmitter release disorder and the like in mammal. As used herein, by the mammal is meant human, dog, cow, horse, rat, mouse and the like.

In order to illustrate the usefulness of the compound (I), the pharmacological test result of the representative compound is shown in the following.

Test Compound

Compound A: 8-(2-((2-pentylcyclopropan-1-yl)methyl)cyclopropyl) octanoic acid (Compound of Example 1)

EXPERIMENTAL EXAMPLE 1

(1) Method

For population spike (PS) recording, the head of a mouse was fixed with ear bars under urethane anesthesia (an initial dose of 1.2 g/kg, i.p. followed by supplemental injections of 0.2-0.6 g/kg as needed), and a glass recording electrode was placed in the cell body layer of dentate granule cells (coordinates=2.0-2.5 mm posterior to bregma, 1.0-1.5 mm lateral to the midline, 1.5-2.0 mm ventral to the brain surface). Initial responses were obtained using cathodal stimulation (7.0-9.0 V, 0.1 Hz, 0.1 ms in duration) of the perforant path. After both stimulating and recording electrodes were properly positioned and population spike was obtained, the baseline was allowed to stabilize for 30 min prior to baseline recording. Body temperature was maintained at 37° C. Compound A was dissolved in 50% polyethylene glycol, diluted with water, and injected intraperitoneally (i.p.) at concentrations of 0.1 mg/kg, 1 mg/kg and 10 mg/kg, respectively. After the intraperitoneal administration of Compound A, the PS amplitude was measured every 5 minutes, and the proportion in percentage of the obtained value to the PS amplitude at the time of the start of i.p. administration of Compound A (% of basal PS amplitude) was calculated.

(2) Results

Compound A (1 mg/kg, i.p.) potentiated PS amplitude to approximately 200% of basal values, being evident still 120 min after injection. A similar potentiation was obtained with a lower concentration of Compound A (0.1 mg/kg, i.p.), but a higher concentration of Compound A (10 mg/kg, i.p.) caused much lesser potentiation (FIG. 1). These findings suggest that a drug (Compound A) induces LTP-like potentiation of synaptic transmission of hippocampal neurotransmission, without titanic stimulation to induce LTP, perhaps in a bell-shaped dose dependent manner. This, therefore, raises the possibility that Compound A could be developed as a cognition-enhancing drug.

The pharmaceutical composition of the present invention can be used in the form of a pharmaceutical preparation, for example, in a solid, semisolid or liquid form, which contains the compound (I) or a pharmaceutically acceptable salt thereof, as an active ingredient, in admixture with a conventional pharmaceutically acceptable carrier such as an organic or inorganic carrier or excipient which is suitable for rectal, pulmonary (nasal or buccal inhalation), ocular, external (topical), oral or parenteral (including subcutaneous, intravenous and intramuscular) administration.

The active ingredient may be compounded, for example, with the usual non-toxic, pharmaceutically acceptable carriers in a solid form such as granule, tablet, dragee, pellet, troche, capsule, or suppository; cream; ointment; aerosol; powder; in a liquid form such as solution, emulsion, or suspension; ingestion; eye drops; and any other form suitable for use. If necessary, there may be included in the above preparation an auxiliary substance such as stabilizing, thickening, wetting, emulsifying and coloring agents; perfumes or buffer; or any other commonly used additives.

The compound (I) or a pharmaceutically acceptable salt thereof is included in the pharmaceutical composition in an amount sufficient to produce a desired effect on the progress or disease state.

For applying the composition to a human being or an animal, it is preferable to apply it by intravenous, intramuscular, pulmonary or oral administration, or insufflation. While the dosage of therapeutically effective amount of the compound (I) varies depending on the age and condition of each individual patient to be treated, in the case of intravenous administration, a daily dose of 0.01-100 mg of the compound (I) per kg weight of a human being or an animal, in the case of intramuscular administration, a daily dose of 0.1-100 mg of the compound (I) per kg weight of a human being of an animal, and in case of oral administration, a daily dose of 0.5-100 mg of the compound (I) per kg weight of a human being or an animal is generally given for the prevention and/or treatment of the aforesaid diseases.

The following Examples are given for the purpose of illustrating the present invention in more detail.

Example 1

(1) To a mixture of linoleic acid methyl ester (2.5 g) and dichloromethane (50 ml), a 0.99M solution of diethylzinc (103 ml) in n-hexane was added under a nitrogen atmosphere. The mixture was cooled in an ice-water bath (−5° C. to 0° C.) and stirred for 1 hour at this temperature. Diodomethane (16.4 ml) was added to the mixture, and the mixture was stirred at ambient temperature overnight. After evaporation in vacuo of the solvent, the reacting mixture was dissolved in a mixture of ethyl acetate (EA) and a saturated aqueous solution of ammonium chloride. The separated organic layer was washed with water and dried over magnesium sulfate. After filtration, the filtrate was concentrated in vacuo. The obtained residue was purified by chromatography on silica gel (eluted with 1% EA in n-hexane). The fractions including 8-(2-((2-pentyl-cyclopropan-1-yl)methyl)cyclopropyl)octanoic acid methyl ester were collected and concentrated in vacuo to give 8-(2-((2-pentylcyclopropan-1-yl)methyl)cyclopropyl)octanoic acid methyl ester (2.81 g) as an oil.

$^1$H-NMR (300 MHz, CDCl$_3$) δ −0.30(m, 2H), 0.6-1.7(m, 34H), 2.31(t, 2H, J=7.5 Hz).

(2) A mixture of 8-(2-((2-pentylcyclopropan-1-yl)methyl)cyclopropyl)octanoic acid methyl ester (4.89 g), 1N aqueous solution (33.4 ml) of lithium hydroxide and dioxane (33 ml) was stirred at 60° C. overnight. The mixture was poured into a mixture of ethyl acetate (EA) and a saturated aqueous solution of ammonium chloride. The separated organic layer was washed with water and dried over magnesium sulfate. After filtration, the filtrate was concentrated in vacuo. The obtained residue was purified by chromatography on silica gel (eluted with 20% EA in n-hexane). The fractions including 8-(2-((2-pentylcyclopropan-1-yl)methyl)cyclopropyl)octanoic acid were collected and concentrated in vacuo to give 8-(2-((2-pentylcyclopropan-1-yl)methyl)cyclopropyl)octanoic acid (4.01 g) as an oil.

$^1$H-NMR (300 MHz, CDCl$_3$) δ −0.30(m, 2H), 0.6-1.7(m, 30H), 1.64(t, 2H, J=7.2 Hz), 2.31(t, 2H, J=7.2 Hz).

Mass Spectrum (m/e): 307(M-H)$^-$, 615(2M-H)$^-$.

Example 2

(1) To a mixture of oxalyl dichloride (18.85 ml) and dichloromethane (60 ml), dimethyl sulfoxide (2.99 ml) was added under a nitrogen atmosphere. The mixture was cooled in an ice-water bath and stirred therein for 15 minutes. 9-Hydroxynonanoic acid methyl ester (2.00 g) was added to the mixture. The mixture was stirred for 1 hour and triethylamine (10.8 ml) was added to the reaction mixture. The reaction mixture was stirred for 1 hour at ambient temperature and poured into a mixture of ethyl acetate (EA) and a saturated aqueous solution of ammonium chloride. The separated organic layer was washed with water and dried over magnesium sulfate. After filtration, the filtrate was concentrated in vacuo. The obtained residue was purified by chromatography on silica gel (eluted with 5% EA in n-hexane). The fractions including 8-formylnonanoic acid methyl ester were collected and concentrated in vacuo to give 8-formylnonanoic acid methyl ester (1.69 g) as an oil.

$^1$H-NMR (300 MHz, CDCl$_3$) δ 1.53(brs, 6H), 1.82(br.t, 4H), 2.52(t, 2H, J=7.5 Hz), 2.64(t, 2H, J=7.5 Hz), 3.87(s, 3H), 9.98(s, 1H).

(2) To a mixture of 2-(1,3-dioxolan-2-yl)ethyltriphenylphosphonium bromide (7.62 g) and tetrahydrofuran (THF, 20 ml), a 1M aqueous solution of sodium bis(trimethylsilyl)amide (16.3 ml) was added under a nitrogen atmosphere. The mixture was cooled in a dry ice-acetonitrile bath, allowed to warm to room temperature and stirred for 30 minutes. The reaction mixture was cooled to −90° C. in a liquid nitrogen-methanol bath, and then a mixture of 8-formylnonanoic acid methyl ester (1.60 g) and THF (10 ml) was added dropwise over 1 minute. The reaction mixture was stirred for 30 minutes, allowed to warm to room temperature and stirred for 2 hours. The reaction mixture was poured into a mixture of ice, ethyl acetate (EA) and a saturated aqueous solution of ammonium chloride. The separated organic layer was washed with water and dried over magnesium sulfate. After filtration, the filtrate was concentrated in vacuo. The obtained residue was purified by chromatography on silica gel (eluted with 10% EA in n-hexane). The fractions including 11-(1,3-dioxolan-2-yl)-9-(Z)-undecenoic acid methyl ester were collected and concentrated in vacuo to give 11-(1,3-dioxolan-2-yl)-9-(Z)-undecenoic acid methyl ester (1.49 g) as an oil.

$^1$H-NMR (300 MHz, CDCl$_3$) δ 1.30(m, 8H), 1.61(m, 2H), 2.04(q, 2H, J=6.9 Hz), 2.30(t, 2H, J=7.5 Hz), 2.43(t, 2H, J=5.4 Hz), 3.67(s, 3H), 3.85(m, 2H), 3.98(m, 2H), 4.88(t, 1H, J=4.8 Hz), 5.4(m, 1H), 5.5(m, 1H).

(3) In the same manner as in Example 1(1) using 11-(1,3-dioxolan-2-yl)-9-(Z)-undecenoic acid methyl ester, 8-((2-((1, 3-dioxolan-2-yl)methyl)cyclopropyl)octanoic acid methyl ester was obtained as an oil (0.44 g).

$^1$H-NMR (300 MHz, CDCl$_3$) δ −0.18(m, 1H), 0.6-0.9(m, 3H), 1.1-1.85(m, 14H), 2.30(t, 2H, J=7.5 Hz), 3.67(s, 3H), 3.85(m, 2H), 3.98(m, 2H), 4.94(t, 1H, J=4.8 Hz).

(4) A mixture of 8-((2-((1,3-dioxolan-2-yl)methyl)cyclopropyl)octanoic acid methyl ester (0.42 g), acetic acid (16 ml) and water (4 ml) was stirred at 60° C. overnight. The reaction mixture was poured into a mixture of ice, diethyl ether and a saturated aqueous solution of sodium hydrogencarbonate. The separated organic layer was washed with water and dried over magnesium sulfate. After filtration, the filtrate was concentrated in vacuo and the obtained residue was purified by chromatography on silica gel (eluted with 5% ethyl acetate in n-hexane). The fractions including 8-(2-(formylmethyl)cyclopropyl)octanoic acid methyl ester were collected and concentrated in vacuo to give 8-(2-(formylmethyl)cyclopropyl)octanoic acid methyl ester (0.11 g) as an oil.

$^1$H-NMR (300 MHz, CDCl$_3$) δ −0.12(m, 1H), 0.7-1.7(m, 15H), 2.31(t, 2H, J=7.5 Hz), 2.3-2.5(m, 2H), 3.67(s, 3H), 9.82(t, 1H, J=2.1 Hz).

(5) In the same manner as in Example 2(2) using 8-(2-(formylmethyl)cyclopropyl)octanoic acid methyl ester, 8-(2-(2-(Z)-octenyl)cyclopropyl)octanoic acid methyl ester was obtained as an oil (88 mg).

$^1$H-NMR (300 MHz, CDCl$_3$) δ −0.12(m, 1H), 0.62(m, 1H), 0.70(m, 2H), 0.89(t, 3H, J=6.9 Hz), 1.15-1.45(m, 16H), 1.6 (m, 2H), 2.0(m, 4H), 2.31(t, 2H, J=7.5 Hz), 3.67(s, 3H), 5.39(m, 1H), 5.45(m, 1H).

(6) In the same manner as in Example 1(2) using 8-(2-(2-(Z)-octenyl)cyclopropyl)octanoic acid methyl ester and 0.5N lithium hydroxide instead of 1N lithium hydroxide, 8-(2-(2-(Z)-octenyl)cyclopropyl)octanoic acid was obtained as an oil (56.3 mg).

$^1$H-NMR (300 MHz, CDCl$_3$) δ −0.25(m, 1H), 0.62(m, 1H), 0.70(m, 2H), 0.89(t, 3H, J=6.9 Hz), 1.15-1.45(m, 16H), 1.6 (m, 2H), 2.0(m, 4H), 2.36(t, 2H, J=7.5 Hz), 5.40(m, 1H), 5.43(m, 1H).

Mass Spectrum (m/e): 587.5 (2M-H)$^-$.

Example 3

In the same manner as in Example 1(2) using 8-((2-octyl)cyclopropyl)octanoic acid 2-(2-(methoxy)ethoxy)ethyl ester, 8-((2-octyl)cyclopropyl)octanoic acid was obtained as an oil (18 mg).

$^1$H-NMR (300 MHz, CDCl$_3$) δ −0.35(m, 1H), 0.5-0.7(m, 3H), 0.88(t, 3H, J=6.9 Hz), 1.05-1.7(m, 26H), 2.35(t, 2H, J=7.5 Hz).

Mass Spectrum (m/e): 295.2 (M-H)$^-$.

Example 4

(1) In the same manner as in Example 1(1) using 9, 12, 15-octadecatrienoic acid ethyl ester, 8-(2-((2-((2-ethylcyclopropan-1-yl)methyl)cyclopropan-1-yl)methyl)cyclopropyl)octanoic acid ethyl ester was obtained.

$^1$H-NMR (300 MHz, CDCl$_3$) δ −0.05(m, 3H), 0.8-2.0(m, 33H), 2.61(t, 2H, J=7.5 Hz), 4.45(q, 2H, J=7.2 Hz).

(2) In the same manner as in Example 1(2) using 8-(2-((2-((2-ethyl-cyclopropan-1-yl)methyl)cyclopropan-1-yl)methyl)cyclopropyl)octanoic acid ethyl ester, 8-(2-((2-((2-ethyl-cyclopropan-1-yl)methyl)cyclopropan-1-yl)methyl)cyclopropyl)octanoic acid was obtained.

$^1$H-NMR (300 MHz, CDCl$_3$) δ −0.048(m, 3H), 0.8-2.0(m, 30H), 2.67(t, 2H, J=7.5 Hz).

Mass Spectrum (m/e): 639.5 (2M-H)$^-$, 319.2 (M-H)$^-$.

Example 5

(1) In the same manner as in Example 1(1) using 5, 8, 11, 14-eicosatetraenoic acid ethyl ester, 8-(2-((2-((2-((2-pentyl-cyclopropan-1-yl)methyl)cyclopropan-1-yl)methyl)cyclopropan-1-yl)methyl)cyclopropyl)butanoic acid ethyl ester was obtained.

$^1$H-NMR (300 MHz, CDCl$_3$) δ −0.059(m, 4H), 0.8-2.2(m, 36H), 2.65(t, 2H, J=7.5 Hz), 4.43(q, 2H, J=6.9 Hz).

(2) In the same manner as in Example 1(2) using 8-(2-((2-((2-((2-pentyl-cyclopropan-1-yl)methyl)cyclopropan-1-yl)methyl)cyclopropan-1-yl)methyl)cyclopropyl)butanoic acid ethyl ester, 8-(2-((2-((2-((2-pentyl-cyclopropan-1-yl)methyl)cyclopropan-1-yl)methyl)cyclopropan-1-yl)methyl)cyclopropyl)butanoic acid was obtained.

$^1$H-NMR (300 MHz, CDCl$_3$) δ −0.25(m, 4H), 0.55-1.7(m, 33H), 2.37(t, 2H, J=7.2 Hz).

Mass Spectrum (m/e): 319 (M-H)$^-$.

Example 6

(1) In the same manner as in Example 1(1) using 6, 9, 12-octadecatrienoic acid ethyl ester, 8-(2-((2-((2-pentyl-cyclopropan-1-yl)methyl)cyclopropan-1-yl)methyl)cyclopropyl)pentanoic acid ethyl ester was obtained.

$^1$H-NMR (300 MHz, CDCl$_3$) δ −0.25(m, 3H), 0.55-1.7(m, 33H), 2.31(t, 2H, J=7.5 Hz), 4.12(q, 2H, J=7.2 Hz).

(2) In the same manner as in Example 1(2) using 8-(2-((2-((2-pentyl-cyclopropan-1-yl)methyl)cyclopropan-1-yl)methyl)cyclopropyl)pentanoic acid ethyl ester, 8-(2-((2-((2-pentyl-cyclopropan-1-yl)methyl)cyclopropan-1-yl)methyl)cyclopropyl)pentanoic acid was obtained.

$^1$H-NMR (300 MHz, CDCl$_3$) δ −0.21(m, 3H), 0.55-1.85 (m, 30H), 2.41(t, 2H, J=7.5 Hz).

Mass Spectrum (m/e): 719.6 (2M-H)$^-$, 359.3 (M-H)$^-$.

The invention claimed is:

1. A method for reducing the severity of dementia that is ameliorated by increasing LTP-like potentiation of synaptic transmission comprising:

administering to a mammalian subject in need thereof an amount of a carboxylic acid compound having one or more cyclopropane rings of the formula (I), or a pharmaceutically acceptable salt thereof, effective to increase LTP-like potentiation of synaptic transmission; wherein formula (I) is:

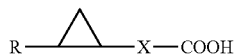

wherein R is alkyl selected from the group consisting of methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, eicosanyl and docosanyl; wherein R may have 1,2-cylcopropylene in a carbon chain and/or cyclopropyl at the end of a chain; or R is:

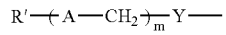

in which

R' is hydrogen or alkyl selected from the group consisting of methyl, ethyl, propyl, isopropyl, butyl, isobutyl, sec-butyl, tert-butyl, and pentyl, Y is a single bond or alkylene, A is 1,2-cyclopropylene or vinylene, and m is an integer from 0 to 5;

wherein the 1,2-cyclopropylene which may be contained in R may have an alkyl selected from the group consisting of methyl, ethyl, propyl, isopropyl, butyl, isobutyl, sec-butyl, tert-butyl, pentyl, tert-pentyl, and hexyl at the 3-position carbon atom;

X is a single bond or alkylene; and the total number of carbon atoms minus the number of cyclopropane ring(s) in the compound of formula (I) is 10-25.

2. The method of claim 1, wherein R is a group selected from:

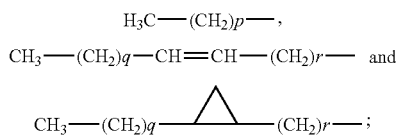

and X is —(CH$_2$)$_{n-}$ ;

wherein n, p, q and r are each an integer, the total of p and n is from 6 to 21, and the total of q, r and n is from 4 to 19.

3. A method for treating a learning or memory disorder that is ameliorated by increasing LTP-like potentiation of synaptic transmission comprising:

administering to a mammalian subject in need thereof an amount of a carboxylic acid compound having one or more cyclopropane rings of the formula (I), or a pharmaceutically acceptable salt thereof effective to increase LTP-like potentiation of synaptic transmission, wherein formula (I) is:

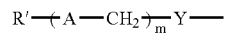

wherein R is alkyl selected from the group consisting of methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, eicosanyl and docosanyl, and the alkyl may have 1,2-cylcopropylene in a carbon chain and/or cyclopropyl at the end of a chain; or R is:

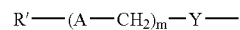

in which

R' is hydrogen or alkyl selected from the group consisting of methyl, ethyl, propyl, isopropyl, butyl, isobutyl, sec-butyl, tert-butyl, and pentyl, Y is a single bond or alkylene, A is 1,2-cyclopropylene or vinylene, and m is an integer from 0 to 5;

in which 1,2-cyclopropylene may have an alkyl selected from the group consisting of methyl, ethyl, propyl, isopropyl, butyl, isobutyl, sec-butyl, tert-butyl, pentyl, tert-pentyl, and hexyl at the 3-position carbon atom;

X is a single bond or alkylene; and the total number of carbon minus the number of cyclopropane ring is 10-25;

or a pharmaceutically acceptable salt thereof.

4. The method of claim 3, wherein R is a group selected from the group consisting of:

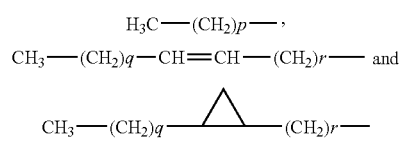

and X is —(CH$_2$)$_{n-}$, in which n, p, q and r are each an integer, the total of p and n is from 6 to 21, and the total of q, r and n is from 4 to 19.

5. The method of claim 3, wherein said subject has a memory disorder ameliorated by increasing LTP-like potentiation of synaptic transmission.

6. The method of claim 3, wherein said subject has a learning disorder ameliorated by increasing LTP-like potentiation of synaptic transmission.

7. A method for treating a disease or disorder that is ameliorated by increasing LTP-like synaptic transmission comprising:

administering to a mammalian subject in need thereof an amount of a compound of formula (I), or a pharmaceutically acceptable salt thereof, effective to increase LTP-like potentiation of synaptic transmission, wherein formula (I) is:

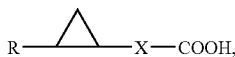 (I)

wherein R is alkyl, which may optionally have one or more 1,2-cyclopropylene in a carbon chain and/or cyclopropyl at the end of a chain, or
R is:

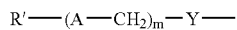

in which
R' is hydrogen or alkyl,
A is 1,2-cyclopropylene or vinylene,
m is an integer from 0 to 5, and
Y is a single bond or alkylene;

in which the 1,2-cyclopropylene which may be contained in R may have an alkyl substituent at the 3-position carbon atom;

X is a single bond or alkylene; and wherein the total number of carbons minus the number of cyclopropane rings in the compound of formula (I) is 10-25;

wherein said disease or disorder that is ameliorated by increasing LTP-like potentiation of synaptic transmission is selected from the group consisting of senile dementia, cerebrovascular dementia, postraumatic dementia, dementia caused by chronic subdural hematoma, dementia caused by normal pressure hydrocephalus, and post-cephalomeningitic dementia.

8. The method of claim 1, wherein said dementia that is ameliorated by increasing LTP-like potentiation of synaptic transmission is selected from the group consisting of senile dementia, cerebrovascular dementia, postraumatic dementia, dementia caused by chronic subdural hematoma, dementia caused by normal pressure hydrocephalus, and post-cephalomeningitic dementia.

* * * * *

UNITED STATES PATENT AND TRADEMARK OFFICE
CERTIFICATE OF CORRECTION

PATENT NO. : 7,468,389 B2  
APPLICATION NO. : 10/450816  
DATED : December 23, 2008  
INVENTOR(S) : Tomoyuki Nishizaki et al.

Page 1 of 1

It is certified that error appears in the above-identified patent and that said Letters Patent is hereby corrected as shown below:

On the title page, Item 73, the Assignees information is incorrect. Item 73 should read as follows:

--(73) Assignees: Tox K.K., Kobe-shi, (JP);  
Tomoyuki NISHIZAKI, Kobe-shi, (JP)--

Signed and Sealed this

Twenty-fourth Day of November, 2009

David J. Kappos  
*Director of the United States Patent and Trademark Office*